US009757100B2

(12) United States Patent
Hibner

(10) Patent No.: US 9,757,100 B2
(45) Date of Patent: *Sep. 12, 2017

(54) BIOPSY DEVICE WITH INTEGRAL VACUUM ASSIST AND TISSUE SAMPLE AND FLUID CAPTURING CANISTER

(71) Applicant: Devicor Medical Products, Inc., Cincinnati, OH (US)

(72) Inventor: John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/266,500

(22) Filed: Sep. 15, 2016

(65) Prior Publication Data

US 2017/0000468 A1    Jan. 5, 2017

Related U.S. Application Data

(63) Continuation of application No. 14/993,645, filed on Jan. 12, 2016, now Pat. No. 9,468,425, which is a
(Continued)

(51) Int. Cl.
*A61B 5/00* (2006.01)
*A61B 10/02* (2006.01)

(52) U.S. Cl.
CPC ...... *A61B 10/0275* (2013.01); *A61B 10/0283* (2013.01); *A61B 2010/0208* (2013.01); *A61B 2010/0225* (2013.01)

(58) Field of Classification Search
CPC . A61B 10/02; A61B 10/0275; A61B 10/0283; A61B 2010/0208; A61B 2010/0225
See application file for complete search history.

(56) References Cited

U.S. PATENT DOCUMENTS 2,853,071 A    9/1958  Saffir
3,630,192 A   12/1971  Jamshidi
(Continued)

FOREIGN PATENT DOCUMENTS

EP    0 890 339    1/1999
EP    0 995 400    4/2000
(Continued)

OTHER PUBLICATIONS

EnCor MRI Specifications and Breast Biopsy System, SenoRx, 2005, pp. 102.
(Continued)

*Primary Examiner* — Max Hindenburg
(74) *Attorney, Agent, or Firm* — Frost Brown Todd LLC

(57) ABSTRACT

A biopsy device includes a body, a probe cannula, a cutter, a vacuum source, a tissue sample holder, and a flexible tube. The probe cannula extends distally from the body and defines an internal passage with a side aperture. The cutter is translatable relative to the probe cannula to sever a tissue sample received in the probe cannula. The vacuum source is in communication with the cutter. The tissue sample holder includes a vacuum port on the exterior surface to communicate with the vacuum source and a removable portion to hold solid tissue samples. The removable portion is selectively removable from the tissue sample holder and includes a straining member to separate fluids from solids. The flexible tube couples the tissue sample holder with the body such that the tissue sample holder is flexibly spaced away from the body.

27 Claims, 7 Drawing Sheets

Related U.S. Application Data continuation of application No. 14/188,744, filed on Feb. 25, 2014, now Pat. No. 9,265,485, which is a continuation of application No. 12/775,780, filed on May 7, 2010, now Pat. No. 8,956,306, which is a continuation of application No. 11/753,952, filed on May 25, 2007, now Pat. No. 7,758,515, which is a continuation-in-part of application No. 10/953,834, filed on Sep. 29, 2004, now abandoned.

(56) References Cited

U.S. PATENT DOCUMENTS

| | | |
|---|---|---|
| 3,719,086 A | 3/1973 | Bannister et al. |
| 3,994,297 A | 11/1976 | Kopf |
| 4,051,852 A | 10/1977 | Villari |
| 4,600,014 A | 7/1986 | Beraha |
| 4,782,833 A | 11/1988 | Einhorn |
| 5,106,364 A * | 4/1992 | Hayafuji .......... A61B 17/32002 30/208 |
| 5,108,381 A | 4/1992 | Kolozsi |
| 5,197,968 A | 3/1993 | Clement |
| 5,234,000 A | 8/1993 | Hakky et al. |
| 5,275,609 A | 1/1994 | Pingleton et al. |
| 5,406,959 A | 4/1995 | Mann |
| 5,409,013 A | 4/1995 | Clement |
| 5,439,457 A | 8/1995 | Yoon |
| 5,505,210 A * | 4/1996 | Clement .......... A61B 10/04 600/566 |
| 5,526,822 A | 6/1996 | Burbank et al. |
| 5,532,168 A | 7/1996 | Marantz |
| 5,575,293 A | 11/1996 | Miller et al. |
| 5,601,585 A | 2/1997 | Banik et al. |
| 5,624,418 A * | 4/1997 | Shepard .......... A61M 1/0056 210/232 |
| 5,645,209 A | 7/1997 | Green et al. |
| 5,649,547 A | 7/1997 | Ritchart et al. |
| 5,769,086 A | 6/1998 | Ritchart et al. |
| 5,775,333 A | 7/1998 | Burbank et al. |
| 5,792,425 A * | 8/1998 | Clark .......... B01D 29/012 210/321.75 |
| 5,873,967 A | 2/1999 | Clark et al. |
| 5,876,329 A | 3/1999 | Harhen |
| 5,928,164 A | 7/1999 | Burbank et al. |
| 5,964,716 A | 10/1999 | Gregoire et al. |
| 5,980,469 A | 11/1999 | Burbank et al. |
| 6,007,497 A | 12/1999 | Huitema |
| 6,017,316 A | 1/2000 | Ritchart et al. |
| 6,042,593 A | 3/2000 | Storz et al. |
| 6,077,230 A | 6/2000 | Gregoire et al. |
| 6,083,177 A | 7/2000 | Kobren et al. |
| 6,086,544 A | 7/2000 | Hibner et al. |
| 6,120,462 A | 9/2000 | Hibner et al. |
| 6,142,946 A | 11/2000 | Hwang et al. |
| 6,142,956 A | 11/2000 | Kortenbach et al. |
| 6,213,957 B1 | 4/2001 | Milliman et al. |
| 6,228,055 B1 | 5/2001 | Foerster et al. |
| 6,231,522 B1 | 5/2001 | Voegele et al. |
| 6,273,862 B1 | 8/2001 | Privitera et al. |
| 6,402,701 B1 | 6/2002 | Kaplan et al. |
| 6,409,970 B1 | 6/2002 | Phifer |
| 6,428,486 B2 | 8/2002 | Ritchart et al. |
| 6,436,054 B1 | 8/2002 | Viola et al. |
| 6,485,436 B1 | 11/2002 | Truckai et al. |
| 6,488,636 B2 | 12/2002 | Bryan et al. |
| 6,527,731 B2 | 3/2003 | Weiss et al. |
| 6,544,194 B1 | 4/2003 | Kortenbach |
| 6,620,111 B2 | 9/2003 | Stephens et al. |
| 6,626,849 B2 | 9/2003 | Huitema et al. |
| 6,638,235 B2 | 10/2003 | Miller et al. |
| 6,659,338 B1 | 12/2003 | Dittmann et al. |
| 6,758,824 B1 | 7/2004 | Miller |
| 6,849,080 B2 | 2/2005 | Lee et al. |
| 6,986,748 B2 | 1/2006 | McAlister et al. |
| 7,025,098 B2 | 4/2006 | Osborne |
| 7,025,732 B2 | 4/2006 | Thompson et al. |
| 7,185,681 B2 | 3/2007 | Romano |
| 7,189,206 B2 | 3/2007 | Quick et al. |
| 7,204,811 B2 | 4/2007 | Kortenbach et al. |
| 7,226,424 B2 | 6/2007 | Ritchart |
| 7,252,641 B2 | 8/2007 | Thompson et al. |
| 7,276,032 B2 | 10/2007 | Hibner |
| 7,278,991 B2 | 10/2007 | Morris et al. |
| 7,351,210 B2 | 4/2008 | Cicenas et al. |
| 7,419,472 B2 | 9/2008 | Hibner et al. |
| 7,442,171 B2 | 10/2008 | Stephens et al. |
| 7,445,739 B2 | 11/2008 | Tsonton et al. |
| 7,470,237 B2 | 12/2008 | Beckman et al. |
| 7,497,833 B2 | 3/2009 | Miller |
| 7,556,622 B2 | 7/2009 | Mark et al. |
| 7,575,556 B2 | 8/2009 | Speeg et al. |
| 7,662,109 B2 | 2/2010 | Hibner |
| 7,740,594 B2 | 6/2010 | Hibner |
| 7,740,596 B2 | 6/2010 | Hibner |
| 7,740,597 B2 | 6/2010 | Cicenas et al. |
| 7,749,172 B2 | 7/2010 | Schwindt |
| 7,753,857 B2 | 7/2010 | Hibner |
| 7,758,515 B2 | 7/2010 | Hibner |
| 7,806,834 B2 | 10/2010 | Beckman et al. |
| 7,819,819 B2 | 10/2010 | Quick et al. |
| 7,828,745 B2 | 11/2010 | McAlister et al. |
| 7,828,748 B2 | 11/2010 | Hibner |
| 7,846,107 B2 | 12/2010 | Hoffman et al. |
| 7,854,706 B2 | 12/2010 | Hibner |
| 7,854,707 B2 | 12/2010 | Hibner et al. |
| 7,867,173 B2 | 1/2011 | Hibner et al. |
| 7,896,817 B2 | 3/2011 | Garrison |
| 7,918,804 B2 | 4/2011 | Monson |
| 7,985,239 B2 | 7/2011 | Suzuki |
| 8,002,713 B2 | 8/2011 | Heske et al. |
| 8,016,772 B2 | 9/2011 | Heske et al. |
| 8,038,627 B2 | 10/2011 | Hibner |
| 8,109,885 B2 | 2/2012 | Heske et al. |
| 8,118,755 B2 | 2/2012 | Hibner et al. |
| 8,177,728 B2 | 5/2012 | Hibner et al. |
| 8,177,729 B2 | 5/2012 | Hibner et al. |
| 8,206,316 B2 | 6/2012 | Hibner et al. |
| 8,235,913 B2 | 8/2012 | Hibner et al. |
| 8,241,226 B2 | 8/2012 | Hibner et al. |
| 8,251,916 B2 | 8/2012 | Speeg et al. |
| 8,262,586 B2 | 9/2012 | Almazan et al. |
| 8,282,573 B2 | 10/2012 | Shabaz et al. |
| 8,485,987 B2 | 7/2013 | Videbaek et al. |
| 8,568,335 B2 | 10/2013 | Monson et al. |
| 8,622,927 B2 | 1/2014 | Parihar et al. |
| 8,702,623 B2 | 4/2014 | Parihar et al. |
| 8,956,306 B2 | 2/2015 | Hibner |
| 9,265,485 B2 | 2/2016 | Hibner |
| 2002/0120212 A1 | 8/2002 | Ritchart et al. |
| 2003/0125639 A1 | 7/2003 | Fisher et al. |
| 2003/0199753 A1 | 10/2003 | Hibner et al. |
| 2005/0049521 A1 | 3/2005 | Miller et al. |
| 2005/0215922 A1 | 9/2005 | Tsonton et al. |
| 2006/0041230 A1 | 2/2006 | Davis |
| 2006/0074344 A1 | 4/2006 | Hibner |
| 2006/0074345 A1 | 4/2006 | Hibner |
| 2007/0112751 A1 | 5/2007 | Pyun |
| 2008/0004545 A1 | 1/2008 | Garrison |
| 2008/0082021 A1 | 4/2008 | Ichikawa et al. |
| 2008/0214955 A1 | 9/2008 | Speeg et al. |
| 2010/0075664 A1 | 3/2010 | Maucksch |
| 2010/0152610 A1 | 6/2010 | Parihar et al. |
| 2010/0160819 A1 | 6/2010 | Parihar et al. |
| 2016/0120520 A1 | 5/2016 | Hibner |

FOREIGN PATENT DOCUMENTS

| | | |
|---|---|---|
| EP | 1 520 518 | 4/2005 |
| EP | 1 642 533 | 4/2006 |
| EP | 1 832 234 | 12/2007 |
| EP | 1 932 482 | 6/2008 |
| GB | 2 018 601 | 10/1979 |
| RU | 2021770 | 10/1994 |
| WO | WO 03/077768 | 9/2003 |

(56) References Cited

FOREIGN PATENT DOCUMENTS

| WO | WO 2004/016177 | 2/2004 |
|---|---|---|
| WO | WO 2004/052179 | 6/2004 |
| WO | WO 2004/052212 | 6/2004 |
| WO | WO 2004/075728 | 9/2004 |
| WO | WO 2006/005342 | 1/2006 |
| WO | WO 2006/124489 | 11/2006 |
| WO | WO 2007/019152 | 2/2007 |
| WO | WO 2007/021904 | 2/2007 |
| WO | WO 2007/112751 | 10/2007 |

OTHER PUBLICATIONS

European Communication dated Jun. 25, 2007 re Application No. EP 05256035.
European Communication dated Mar. 19, 2009 re Application No. EP 07250926.
European Search Report and Written Opinion dated Dec. 1, 2005 re Application No. EP 05256035.
European Search Report and Written Opinion dated Jun. 13, 2007 re Application No. EP 07250402.
European Search Report and Written Opinion dated Nov. 14, 2007 re Application No. EP 07250926.
European Search Report and Written Opinion dated Dec. 20, 2007 re Application No. EP 07253220.
European Search Report and Written Opinion dated Apr. 3, 2009 re Application No. EP 08252518.
European Search Report and Written Opinion dated Apr. 3, 2009 re Application No. EP 08252524.
European Search Report and Written Opinion dated Sep. 29, 2010 re Application No. EP 10251076.
European Search Report and Written Opinion dated Apr. 23, 2012 re Application No. EP 11193357.
European Written Opinion dated Apr. 26, 2010 re Application No. EP 08252524.
Supplementary European Search Report and Written Opinion dated Dec. 16, 2009 re Application No. EP 06789155.
International Preliminary Report on Patentability dated Feb. 5, 2008 re Application No. PCT/US2006/030022.
International Search Report and Written Opinion dated Sep. 27, 2007 re Application No. PCT/US2006/030022.
International Search Report and Written Opinion dated Dec. 18, 2008 re Application No. PCT/US2008/058627.
US Office Action, Non-Final Rejection dated Mar. 20, 2008 re U.S. Appl. No. 11/782,963.
US Office Action, Final Rejection dated Sep. 26, 2008 re U.S. Appl. No. 11/782,963.
US Office Action, Non-Final Rejection dated Apr. 4, 2008 re U.S. Appl. No. 11/736,117.
US Office Action, Non-Final Rejection dated Oct. 6, 2008 re U.S. Appl. No. 11/736,117.
U.S. Appl. No. 60/869,736, filed Dec. 13, 2006.
U.S. Appl. No. 60/874,792, filed Dec. 13, 2006.

\* cited by examiner

BIOPSY DEVICE WITH INTEGRAL VACUUM ASSIST AND TISSUE SAMPLE AND FLUID CAPTURING CANISTER

CROSS REFERENCE TO RELATED APPLICATIONS

The present application is a continuation of co-pending and commonly-owned U.S. patent application Ser. No. 14/993,645, entitled "BIOPSY DEVICE WITH INTEGRAL VACUUM ASSIST AND TISSUE SAMPLE AND FLUID CAPTURING CANISTER," published as U.S. Pat. Publ. No. 2016/0120520 on May 5, 2016, which is a continuation of U.S. patent application Ser. No. 14/188,744, entitled "BIOPSY DEVICE WITH INTEGRAL VACUUM ASSIST AND TISSUE SAMPLE AND FLUID CAPTURING CANISTER," issued as U.S. Pat. No. 9,265,485 on Feb. 23, 2016, which is a continuation of U.S. patent application Ser. No. 12/775,780, entitled "BIOPSY DEVICE WITH INTEGRAL VACUUM ASSIST AND TISSUE SAMPLE AND FLUID CAPTURING CANISTER" to Hibner, filed on May 7, 2010, issued as U.S. Pat. No. 8,956,306 on Feb. 17, 2015, which is a continuation of U.S. patent application Ser. No. 11/753,952, "BIOPSY DEVICE WITH INTEGRAL VACUUM ASSIST AND TISSUE SAMPLE AND FLUID CAPTURING CANISTER" to Hibner, et al. filed on May 25, 2007, issued as U.S. Pat. No. 7,758,515 on Jul. 20, 2010, which is a continuation in part of U.S. patent application Ser. No. 10/953,834, "BIOPSY APPARATUS AND METHOD" to Hibner et al., filed 29 Sep. 2004, published as U.S. Pat. Publ. No. 2006/0074345 on Apr. 6, 2006, and the disclosures of which are hereby incorporated by reference in their entirety.

FIELD OF THE INVENTION

The present invention relates in general to biopsy devices, and more particularly to biopsy devices having a cutter for severing tissue, and even more particularly to biopsy devices for multiple sampling with a probe remaining inserted

BACKGROUND OF THE INVENTION

When a suspicious tissue mass is discovered in a patient's breast through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

An open biopsy is performed by making a large incision in the breast and removing either the entire mass, called an excisional biopsy, or a substantial portion of it, known as an incisional biopsy. An open biopsy is a surgical procedure that is usually done as an outpatient procedure in a hospital or a surgical center, involving both high cost and a high level of trauma to the patient. Open biopsy carries a relatively higher risk of infection and bleeding than does percutaneous biopsy, and the disfigurement that sometimes results from an open biopsy may make it difficult to read future mammograms. Further, the aesthetic considerations of the patient make open biopsy even less appealing due to the risk of disfigurement. Given that a high percentage of biopsies show that the suspicious tissue mass is not cancerous, the downsides of the open biopsy procedure render this method inappropriate in many cases.

Percutaneous biopsy, to the contrary, is much less invasive than open biopsy. Percutaneous biopsy may be performed using fine needle aspiration (FNA) or core needle biopsy. In FNA, a very thin needle is used to withdraw fluid and cells from the suspicious tissue mass. This method has an advantage in that it is very low-pain, so low-pain that local anesthetic is not always used because the application of it may be more painful than the FNA itself. However, a shortcoming of FNA is that only a small number of cells are obtained through the procedure, rendering it relatively less useful in analyzing the suspicious tissue and making an assessment of the progression of the cancer less simple if the sample is found to be malignant.

During a core needle biopsy, a small tissue sample is removed allowing for a pathological assessment of the tissue, including an assessment of the progression of any cancerous cells that are found. The following patent documents disclose various core biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al.

At present, a biopsy instrument marketed under the trade name MAMMOTOME is commercially available from ETHICON ENDO-SURGERY, INC. for use in obtaining breast biopsy samples. This device generally retrieves multiple core biopsy samples from one insertion into breast tissue with vacuum assistance. In particular, a cutter tube is extended into a probe to cut tissue prolapsed into a side aperture under vacuum assistance and then the cutter tube is fully retracted between cuts to extract the sample, deposited upon an externally exposed surface accessible by a grasping instrument.

With a long probe, the rate of sample taking is limited not only by the time required to rotate or reposition the probe but also by the time needed to translate the cutter. As an alternative to this "long stroke" biopsy device, a "short stroke" biopsy device is described in the following commonly assigned patent applications: U.S. patent application Ser. No. 10/676,944, "Biopsy Instrument with Internal Specimen Collection Mechanism" filed Sep. 30, 2003 in the name of Hibner et al. The cutter is cycled across the side aperture, reducing the sample time. Several alternative specimen collection mechanisms are described that draw samples through the cutter tube, all of which allow for taking multiple samples without removing the probe from the breast.

In particular, in the cross referenced U.S. patent application Ser. No. 10/953,834, "BIOPSY APPARATUS AND METHOD", these tissue samples are drawn by vacuum proximally through the cutter tube into a serial tissue stacking assembly that preserves the order of sample taking can be visually observed through a transparent lumen, and can serve as a transport container for samples taken during a pathology examination.

Some clinicians prefer to capture a plurality of biopsy samples in a small canister attached to a proximal end of the biopsy instrument, such as described in U.S. Pat. No. 6,638,235 to Miller and U.S. Pat. Appl. Publ. No. 2006/0260994 to Mark. Vacuum draws these samples into the canister while allowing fluids to pass through tubing back to a fluid capturing receptacle. Periodically, the canister is disengaged from the biopsy instrument for removing each sample and sending to pathology professionals for assessment.

While these known tissue storage approaches have a number of advantages, bodily tissues and fluids present a biological hazard to medical personnel that must be controlled while not interfering with the efficiency of the biopsy procedure.

SUMMARY OF THE INVENTION

The present invention addresses these and other problems of the prior art by providing a biopsy device that has a probe cannula that is inserted into tissue to obtain a core biopsy sample by translating a cutter with the probe cannula. A pneumatic pressure differential is used to draw a severed tissue sample proximally from the probe cannula into a biopsy sample and fluid capturing canister sized to complete a full biopsy and therapy procedure and to provide a convenient method of transporting the same to a pathology professional for sample assessment. Contact with the biopsy samples and extracted bodily fluids is avoided in that the container need not be opened in a biopsy suite. In addition, the overall volume of single patient use disposable items is reduced by combining the fluid collection and sample collection containers into a single reservoir, thereby reducing the volume of product inventory and biohazard waste materials.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

Figure 1:
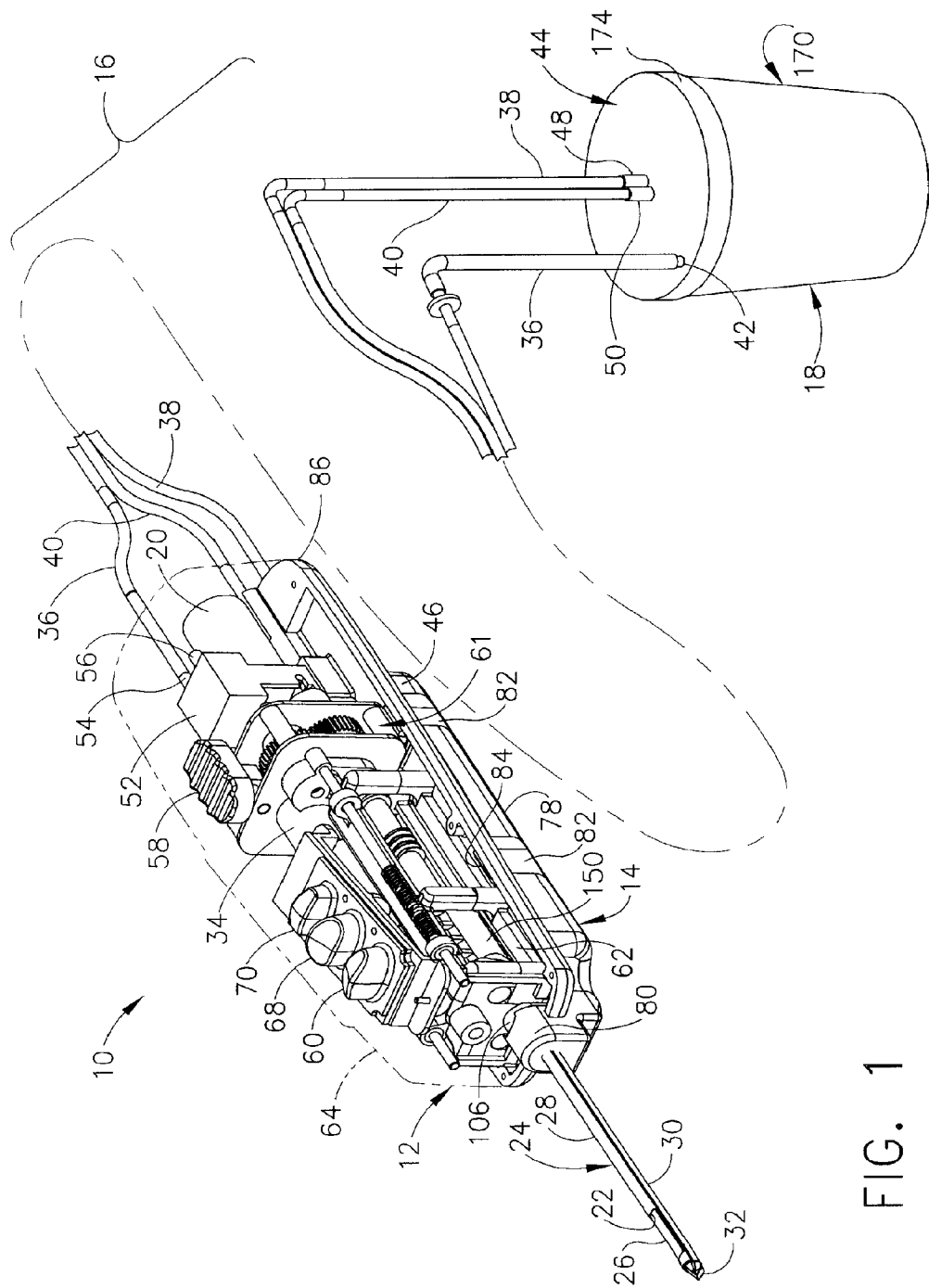
FIG. 1 is an isometric view of a self-contained biopsy system including a biopsy device with cover omitted in fluid communication with the biopsy sample and fluid capturing canister.
Figure 6:
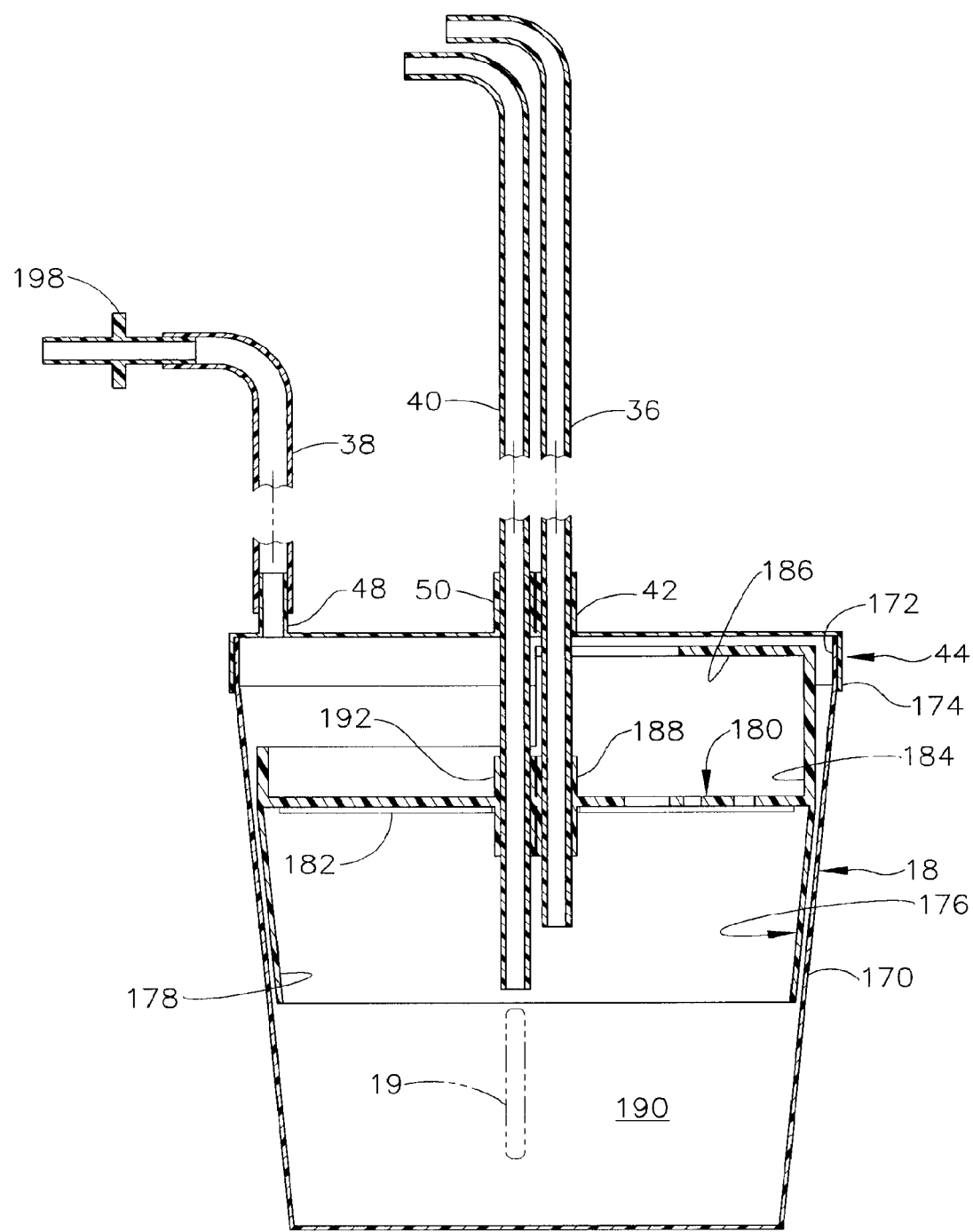
FIG. 6 is a vertical cross section bisecting the biopsy sample and fluid capturing canister of FIG. 1.

Turning to the Drawings, wherein like numerals denote like components throughout the several views, in FIG. 1, a biopsy device 10 includes a reusable handpiece 12 and a disposable probe assembly 14. A self-contained biopsy system 16 is formed by attaching a replaceable biopsy sample and fluid capturing canister 18. The canister 18 is generally sized to accommodate comfortably a volume of fluid that would be extracted, including saline flushing during a biopsy procedure with sufficient internal volume as well to hold biopsy tissue samples 19 (FIG. 6). As such, biohazards associated with bodily tissue and fluids are mitigated in that all such materials are readily transported from a biopsy suite for pathology assessment without the necessity of on-site access.

Tissue is drawn by vacuum assistance generated by vacuum pump 20 integral to the reusable handpiece 12 into a side aperture 22 of a probe cannula 24 of the disposable probe assembly 14. The pneumatic vacuum assistance is achieved via a cutter tube 26 (exposed in the side aperture 22) that translates within a cutter lumen 28 of the probe cannula 24 and via an underslung lateral lumen 30 that distally communicates to the cutter lumen 28 through holes or apertures (not shown) just proximal to a piercing tip 32 of the probe cannula 24. A DC motor 34 in the reusable handpiece 12 powers rotation and translation of the cutter tube 26 to effect the severing.

The disposable probe assembly 14 responds to the position of the cutter tube 26 by sequencing pneumatic communication between the biopsy probe device 10 and the replaceable canister 18 via a vacuum supply line 36, a needle vacuum line 38, and a sample retraction line 40. The vacuum supply line 36 receives vacuum pressure at its distal end from the vacuum pump 20 and proximally passes through and proximally is engaged over a hose nib 42 formed onto the canister lid 44 of the canister 18. The needle vacuum line 38 distally communicates to a pneumatic sequencing spool valve 46 in the disposable probe assembly 14 and is frictionally held within a first protruding cylindrical hose receptacle 48 formed onto a canister lid 44 of the canister 18. The sample retraction line 40 distally communicates to the disposable probe assembly 14 and proximally passes through and is frictionally held within a second protruding cylindrical hose receptacle 50.

The reusable handpiece 12 includes a pneumatic manifold 52 having an upper right port 54 connected to the vacuum supply line 36 and an upper left port 56 open to atmosphere. It should be appreciated that the manifold 52 serves as a mounting for the vacuum pump 20 that generates the pressure differential between the ports 54, 56.

Figure 2:
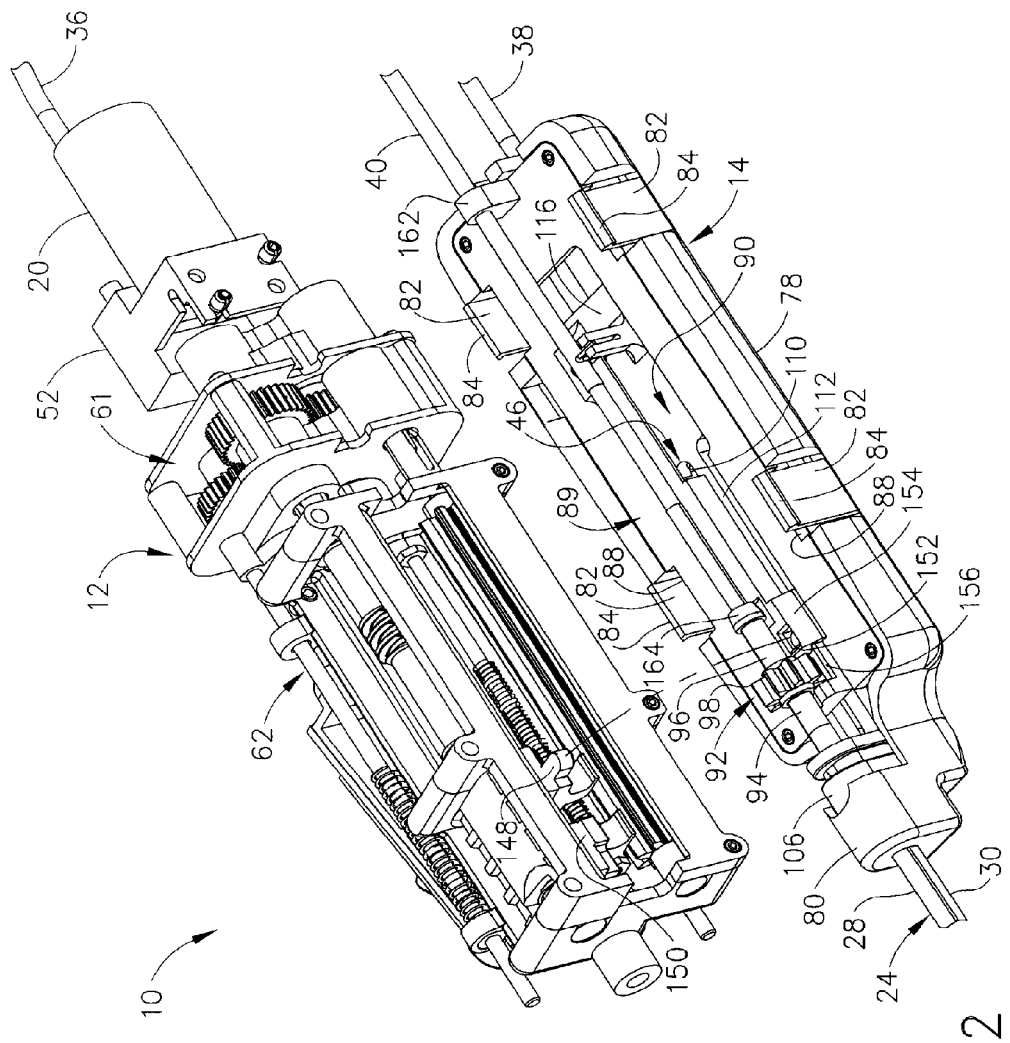
FIG. 2 an isometric view of the biopsy device of FIG. 1 with the cover and lower handle tray omitted and a reusable handpiece disengaged from a disposable probe assembly.

With particular reference to FIGS. 1-2, insertion of the probe cannula 24 into tissue is integrally supported by the piercing tip 32 attached at the distal end as well as a longitudinal jack hammer motion to the probe cannula 24 selected by positioning a slide button 58 distally and depressing a forward motor button 60. In response, the DC motor 34 drives a transmission section 61 grounded to a top cover 64 (depicted in phantom in FIG. 1) of the reusable handpiece 12 to longitudinally reciprocate an internal carriage frame assembly 62 that is engaged for movement with the probe cannula 24. With the slide button 58 proximally positioned, depression of the forward motor button 60 causes the DC motor 34 to advance and rotate the cutter tube 26, depicted in FIG. 1 as having been fully distally translated, closing the side aperture 20. Depression of a reverse motor button 68 causes the cutter tube 26 to retract. Depression of a mode button 70 may cause other functions to be performed. An additional feature contemplated but not depicted includes using the mode button 70 to selectively communicate a saline supply to the lateral lumen 30 to flush the probe cannula 24. It should be appreciated that the biopsy device 10 includes a minimum of "tethers" that would impede use, pose a tripping hazard, prevent use in an austere clinical setting, or extend set-up time.

Alternatively, instead of "hard-walled" lateral lumen 30 separated from the cutter lumen 28 along its length, applications consistent with the present invention may have a cylindrical probe cannula (not depicted) wherein the cutter tube 26 is positioned off-center to translate across a side aperture. A "soft-walled" lateral lumen may then be defined as a space between an outer diameter of the cutter tube and an inner diameter of the cylindrical probe cannula.

In FIGS. 1-4, the disposable probe assembly 14 has a bottom cover 78 with a distal probe mount cover 80 that assists in supporting the probe cannula 24 while allowing the longitudinal jack hammer motion. A plurality of locking tabs 82 with locking edges 84 extend upwardly through pass-through slots (not shown) formed in the periphery of a lower handle tray 86 (FIG. 1) attached to the cover 64 of the reusable handpiece 12 to resiliently extend outwardly into engaging contact with the slots facilitating replacement of the disposable probe assembly 14. Relieved areas 88 are formed behind each locking tab 82 in a top extension member 89 that surrounds a probe support body 90. The combination covers a cavity defined by the bottom cover 78, which allows depression of the locking tabs 82 to unlock the disposable probe assembly 14 to install another identical or similar assembly.

A proximal end of the cutter tube 26 receives a cutter gear 92 having distal and proximal reduced diameter bearing surfaces 94, 96 on each longitudinal side of a rotation spur gear section 98, which engage the reusable handpiece 12 for rotation and for longitudinal translation through a distally open longitudinal aperture 100 (FIG. 3) formed in the bottom cover 78.

Figure 3:
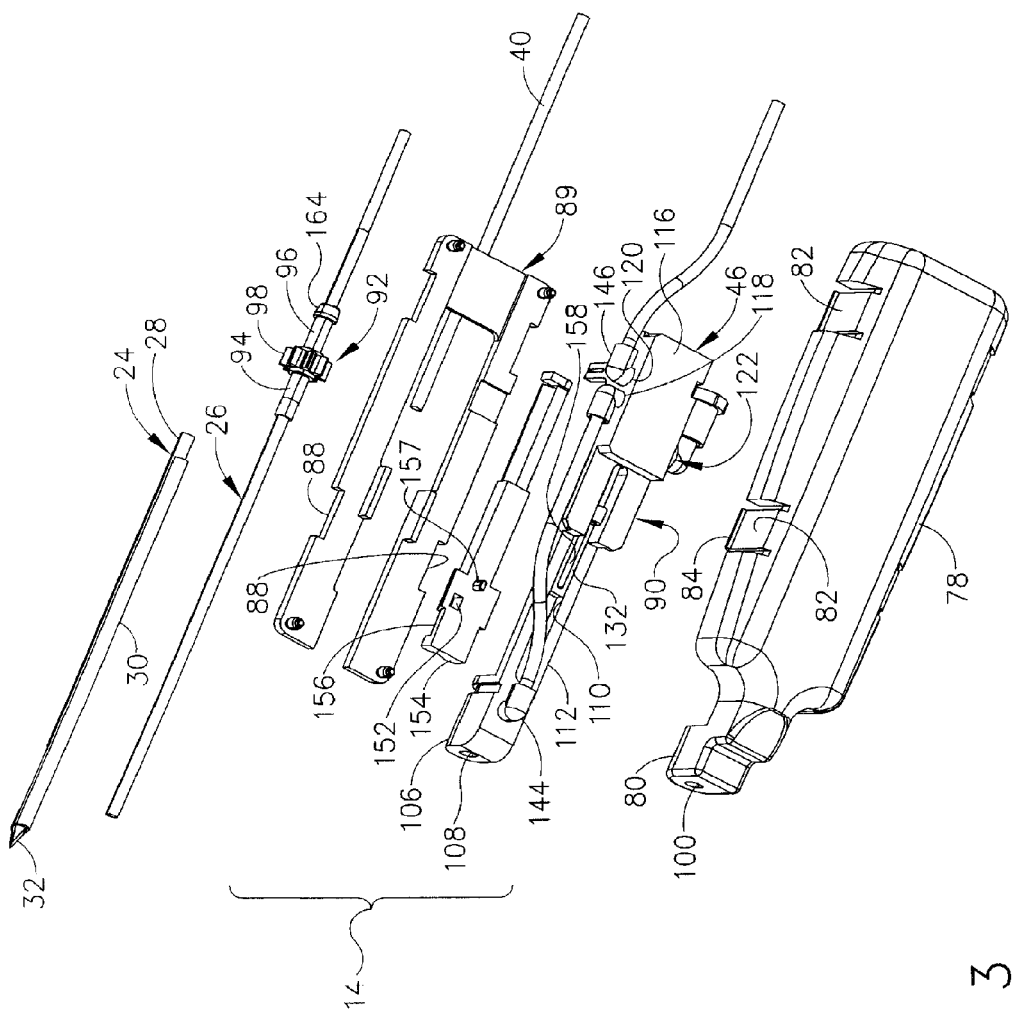
FIG. 3 an exploded view from below, left of the disposable probe assembly of FIG. 2.
Figure 4:
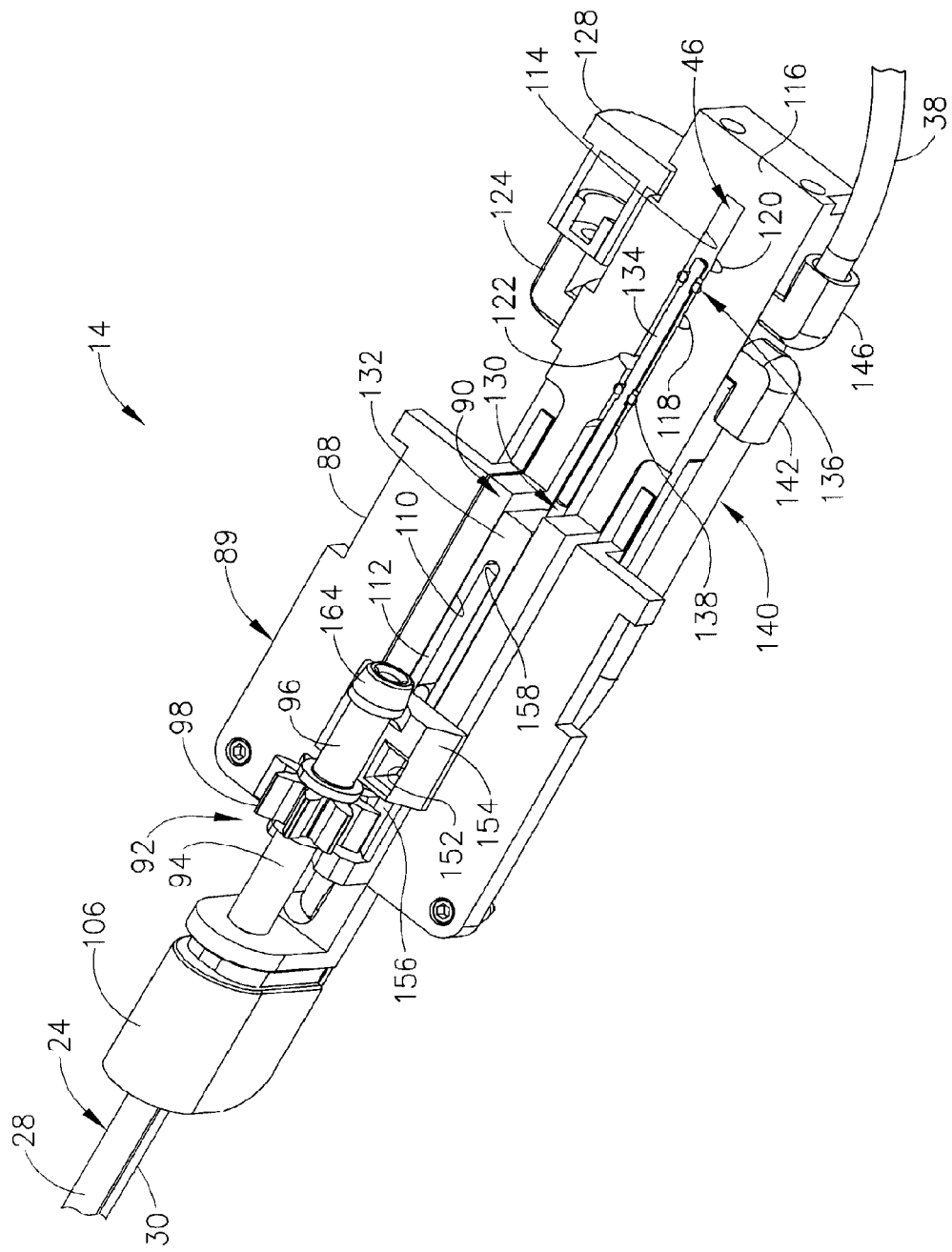
FIG. 4 is an isometric view from left, aft of the disposable probe assembly of FIG. 2 cut away to expose a pneumatic sequencing spool valve.

In FIGS. 2-4, the disposable probe assembly 14 has movable components that respond to the actuating motions of the reusable handpiece 12. The probe support body 90 includes a distal probe mount 106 that is received within the distal probe mount cover 80 of the bottom cover 78. Proximal to and underlying a longitudinal axis of the disposable probe assembly 14 defined by a probe guide hole 108 passing through the distal probe mount 106, a vertically open longitudinal slot 110 is formed into a necked portion 112 of the probe support body 90.

With particular reference to FIGS. 3-4, at a proximal end of the longitudinal trough 110, a distally open, longitudinally aligned valve bore 114 is formed in a proximal block portion 116 of the probe support body 90. Central and proximal ports 118, 120 communicate with the valve bore 114 laterally from a left side of the proximal block portion 116 and a distal port 122 communicates laterally from a right side of the proximal block portion 116. A right distal ninety-degree fitting 124 communicates between the distal port 122 and an intake filter 128.

A valve control rod 130 has a prismatic distal actuating portion 132 extending distally out of the valve bore 114 constrained for only longitudinally movement within the longitudinal slot 110. The valve control rod 130 also has a valve spool portion 134 that longitudinally translates within the valve bore 114 to selectively position between a first position and a second position. A proximal O-ring 136 near a proximal end of the valve spool portion 134 and a distal O-ring 138 are spaced such that the first position entails the O-rings 136, 138 bracketing the central and distal ports 118, 122 (i.e., distal position of the valve control rod 130) and the second position entails the O-rings 136, 138 bracketing the proximal and central ports 120, 118, respectively (i.e., proximal position of the valve control rod 130).

A distal vacuum conduit 140 has one end attached to a center ninety-degree fitting 142 attached to the central port 118 and the other end attached to a probe union ninety-degree fitting 144 that communicates with the lateral lumen 30. The needle vacuum line 38 has its distal end attached to a proximal ninety degree fitting 146 attached to the proximal port 120.

A front actuation finger 148 (FIG. 2) of a front carriage 150 is received within an upwardly open socket 152 formed on a left side of a vacuum control shuttle 154 having a lateral concave recessed band 156 shaped to encompass with a clearance a lower portion of the rotation spur gear section 98 of the cutter gear 92. The vacuum control shuttle 154 is laterally sized to bridge the longitudinal slot 110 with a downwardly projecting vacuum actuator lug 157 (FIG. 3) attached to an underside of the shuttle 154 that is received within a vertically open elongate delay slot 158 of the distal actuating end 132 of the vacuum control rod 130. Thus, the rather long cutter travel is translated into a smaller valve movement as the shuttle reaches either full proximal or full distal travel.

A sample retraction line 40 is proximally held by a tube guide 162 extending inwardly from proximal end of the top extension member 89 of the disposable probe assembly 14. A distal end of the longitudinally aligned sample retraction line 40 is received through a rear dynamic seal 164 attached to a proximal end of the cutter gear 92, and into the cutter tube 26.

The reusable handpiece 12 of the biopsy device 10 is substantially as described in greater detail in four commonly-owned and co-pending U.S. patent applications (1) Ser. No. 11/198,558, "Biopsy Device With Replaceable Probe And Incorporating Vibration Insertion Assist And Static Vacuum Source Sample Stacking Retrieval" to Hibner et al., filed 8 Aug. 2005, published as US 2007-0032741 A1; (2) Ser. No. 11/736,117, "Tissue Sample Revolver Drum Biopsy Device" to Hibner et al., filed 17 Apr. 2007; (3) Ser. No. 11/753,665, "Tissue Sample Serial Capturing Biopsy Device" to Hibner, filed 25 May 2007; and (4) Ser. No. 11/465,143 "Vacuum Syringe Assisted Biopsy Device" to Hibner, filed 17 Aug. 2006, published as US 2007-0032743 A1, the disclosures of all of which are hereby incorporated by reference in their entirety. An aft carriage is omitted from the illustrative version for clarity as not being necessary, although a common reusable handpiece may include a second carriage for mounting to other types of disposable probe assemblies as described in the cross referenced applications.

Figure 5:
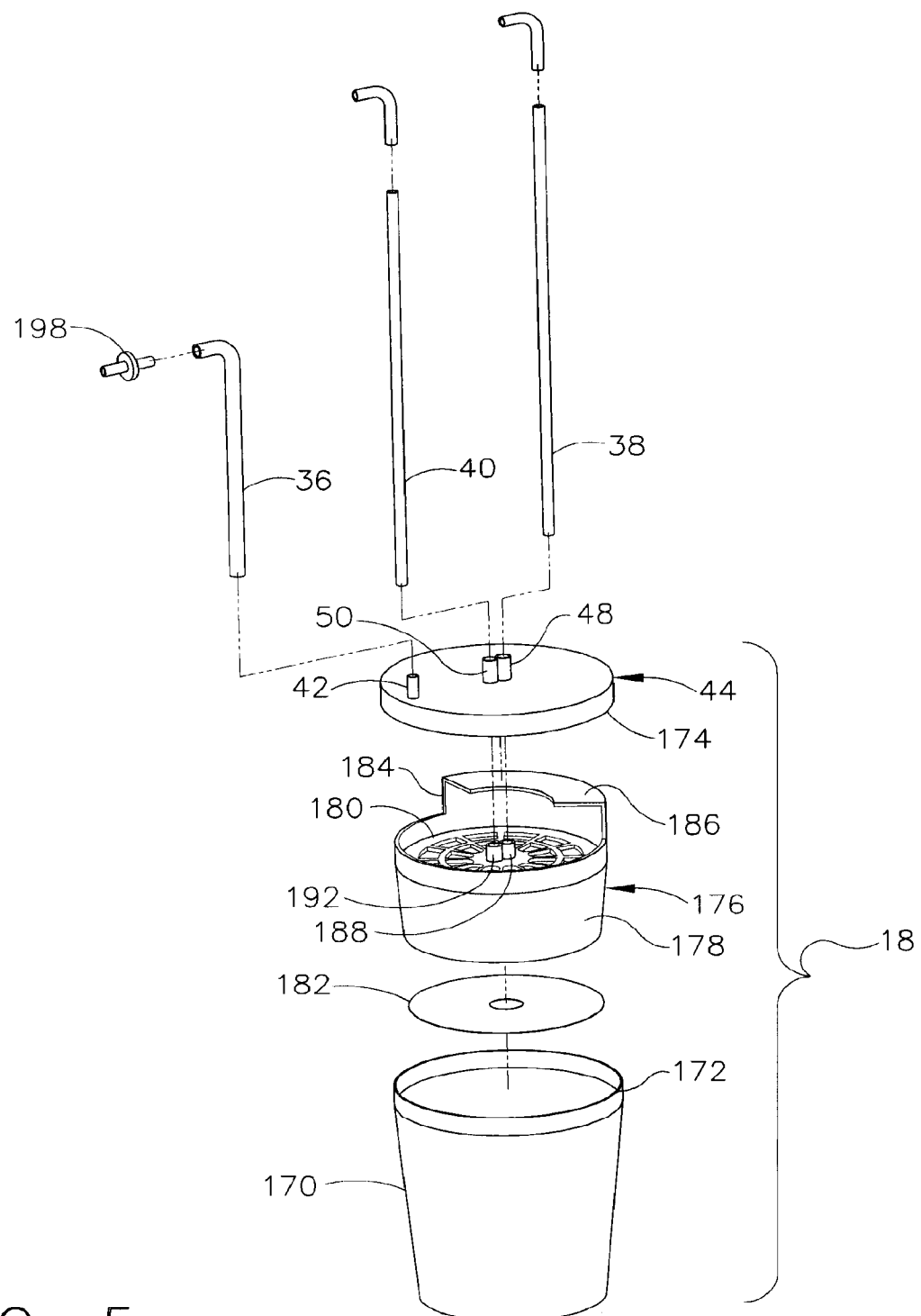
FIG. 5 is an exploded view of the biopsy sample and fluid capturing canister of FIG. 1.

In FIGS. 5-6, the biopsy sample and fluid capturing canister 18 has a tapered cylindrical fluid container 170 whose upper band-shaped lip seals 172 to and is encompassed by a downward circumferential lip 174 of the canister lid 44. A sample collector basket 176 has tapered cylindrical sides 178 shaped to come to rest at approximately a midpoint of the interior of the fluid container 170. Near the top of the tapered cylindrical sides 178 of the sample collector basket 176, a perforated disk 180 is horizontally attached to serve as support to a filter disk 182 adhered to an undersurface. The combination acts in a similar fashion to a drip coffee filter basket. About approximately a third of the upper circumference of the cylindrical sides 178 of the sample collector basket 176, a raised side wall portion 184 culminates in a horizontal and inwardly projecting annular ring portion 186 that serves as a handle for drawing the sample collector basket 176 out of the fluid container 170.

The center of the perforated disk 180 of the sample collector basket 176 includes a first hose receptacle 188 registered for the needle vacuum line 38 to pass on downward into a fluid collection reservoir 190 formed within the fluid container 170 below the perforated disk 180 of the sample collector basket 176. The center of the perforated disk 180 of the sample collector basket 176 also includes a second hose receptacle 192 registered for the sample retraction line 40 to pass on downward into the fluid collection reservoir 190. It should be appreciated that caps or a closed lid (not shown) may be used to seal the biopsy sample and fluid capturing canister 18 after the lines 36, 38, 40 are removed.

With reference to FIGS. 4 and 6, in use, the cutter 26 is initially distally positioned as the probe cannula 24 is inserted into tissue. The vacuum motor 20 operates providing a low pressure within the fluid collection reservoir 190 inside of the replaceable canister 18 via vacuum supply line 36. A hydrophobic filter 198 prevents fluids from reaching the vacuum motor 20. The low pressure communicates to the cutter tube 26 via the sample retraction line 40. After the probe cannula 24 is inserted into tissue beside a suspicious lesion, the cutter tube 26 is retracted. The spool valve 46 is in the first position, with the vacuum lumen 30 vented to atmosphere via central port 118 and distal port 122. The retraction of the cutter gear 92 causes the shuttle 154 to retract correspondingly with its downward lug 152 moving within the delay slot 158 of the distal actuating portion 132 of the valve control rod 130. Once the carriage 150 of the reusable handpiece 12 reaches full proximal travel, the lug 157 contacts the proximal end of the delay slot 158 and changes the pneumatic sequencing spool valve 46 from the first position to the second position. Thus, the vacuum lumen 30 is also exposed to vacuum via central and proximal ports 118, 120 of the spool valve 46 that communicates via the needle vacuum line 38 to the replaceable container 18, exposing the suspicious lesion to the vacuum assistance from both lines 38, 40 to prolapse tissue into the side aperture 20. The spool valve 46 stays in this configuration as the cutter tube 26 is advanced distally while rotating to sever the tissue sample 19. As the shuttle 154 approaches its distal-most position, the lug 157 contacts the distal end of the delay slot 158 of the distal actuating portion 132 of the valve control rod 130, changing to the first position wherein the vacuum lumen 30 is vented to atmosphere and the tissue sample 19 is retracted into the replaceable container 18 by vacuum pressure via the sample retraction line 40.

Once tissue samples 19 are collected in the replaceable container 18, the replaceable container 18 is removed from the biopsy device 10 and transported to a pathology professional for sample assessment.

Alternately, the bodily fluids are drained from the container and replaced with tissue preparation fluid (e.g. Formalin) prior to being sent off for pathological assessment. The bodily fluids are removed from the replaceable canister 18 by removing the canister lid 44, needle vacuum line 38, and the sample retraction line 40 from the replaceable canister assembly 18. While supporting the tapered cylindrical fluid container 170 and the annular ring portion 186 located on sample collector basket 176, the fluids are poured from the tapered cylindrical fluid container 170 with the tissue samples 19 remaining in the tapered cylindrical fluid container 170. The sample collector basket 176 and attached filter disk 182 are then removed form the tapered cylindrical fluid container 170 and tissue preparation fluid (e.g. Formalin) is poured into the tapered cylindrical fluid container 170. A canister lid (not shown) without hose receptacles or nibs is attached to the tapered cylindrical fluid container 170 prior to transporting to a pathology professional for sample assessment. Alternately, after the fluids are poured from the tapered cylindrical fluid container 170, the sample collector basket 176, and attached filter disk 182 are removed from the tapered cylindrical fluid container 170. The tissue samples 19 are transferred from the tapered cylindrical fluid container 170 into a container (not shown) containing tissue preparation fluid (e.g. formalin) prior to transportation to a pathology professional for sample assessment.

Figure 7:
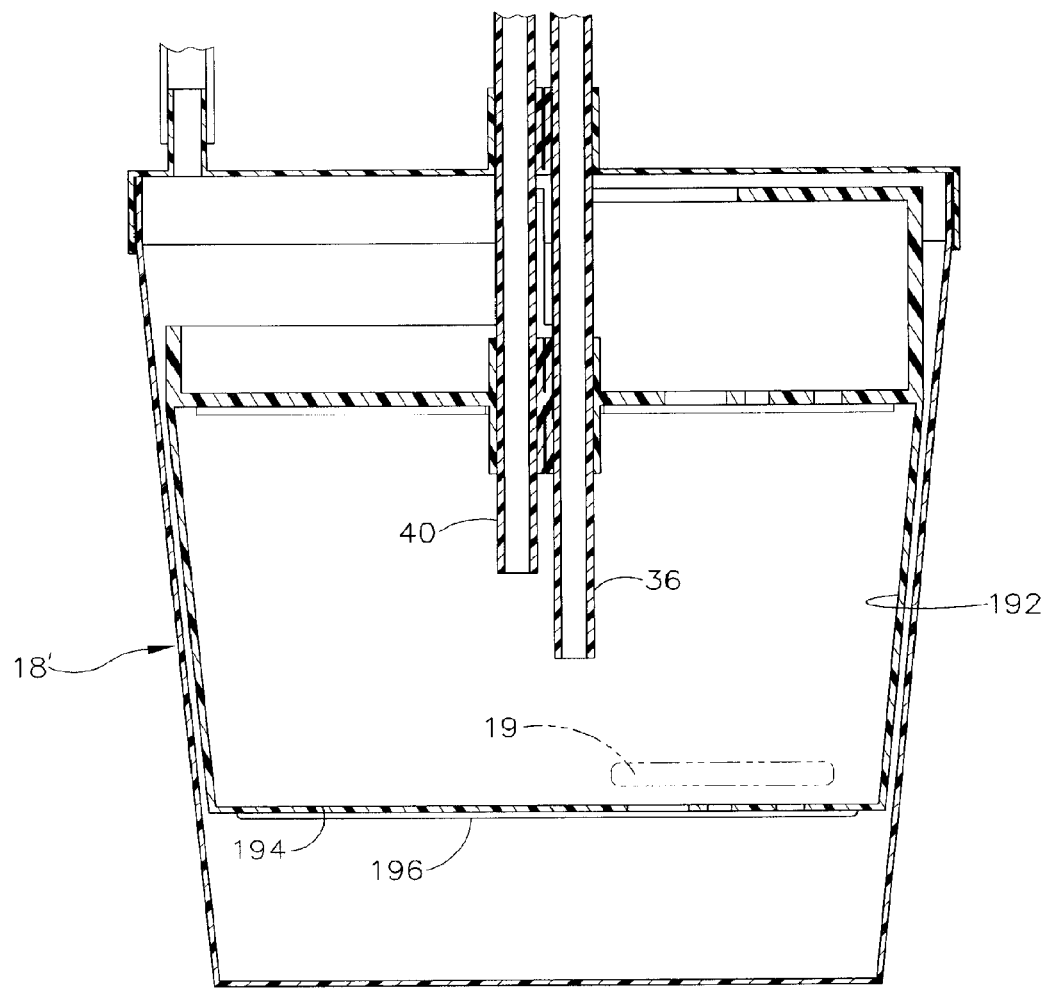
FIG. 7 is a vertical cross section bisecting an alternative biopsy sample and fluid capturing canister for the biopsy system of FIG. 1.

Another alternate embodiment of a biopsy sample and fluid capturing canister 18' is depicted in FIG. 7 as including a fully enclosed sample collector basket 192 with a lower perforated disk 194 and filter 196 to fully contain the tissue samples 19 as they exit sample retraction line 40. The lower perforated disk 194 and filter 196 act to separate the tissue samples 19 from bodily fluids. Once tissue samples 19 are collected in the replaceable container 18, the fully enclosed sample collector basket 192 can be removed form the replaceable container 18 and placed directly into a container (not shown) containing tissue preparation fluid (e.g. Formalin) prior to transportation to a pathology professional for sample assessment.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While preferred embodiments of the present invention have been shown and described herein, it will be obvious to those skilled in the art, given the benefit of the present disclosure, that such embodiments are provided by way of example only. Numerous variations, changes, and substitutions will now occur to those skilled in the art without departing from the spirit and scope of the appended claims.

For example, as a means to further reduce the size and weight of the overall biopsy device 10, the DC motor 34 employed to rotate and translate the cutter tube 26 can also drive the vacuum pump 20 via appropriate gearing.

For another example, although the integral vacuum pump advantageously makes the biopsy device 10 more self-sufficient in austere clinical situations, applications consistent with aspects of the invention may employ a separate vacuum source.

As another example, while a DC motor integral to the reusable handpiece has certain advantages in the illustrative version, applications consistent with aspects of the invention may utilize a motor comprising materials compatible with use in a strong magnetic environment (e.g., magnetic resonance imaging) or remotely placed (e.g., via a drive cable).

As another example, while a pneumatically closed system between the replaceable container 18 and the biopsy device 10 provides various advantages, applications consistent with aspects of the invention may provide separate vacuum source connections to the biopsy device and to the replaceable container 18.

What is claimed is:

1. A biopsy device comprising:
   (a) a probe cannula defining an internal passage and having a side aperture;
   (b) a cutter translatable relative to the probe cannula to sever a tissue sample received in the probe cannula;
   (c) a vacuum source in communication with the cutter;
   (d) a container, wherein the container includes a tissue sample holder located in the container, wherein the tissue sample holder is configured to capture solid tissue samples while allowing fluid to escape the tissue sample holder, wherein the tissue sample holder is configured to hold the solid tissue samples within the container; and
   (e) a conduit, wherein the conduit is configured to provide fluid communication between the container and a proximal end of the cutter, wherein the conduit is further configured to communicate solid tissue samples from the cutter to the tissue sample holder, wherein at least a portion of the conduit includes a flexible tube coupling the container with the probe cannula such that the probe cannula is movable relative to the container, wherein the conduit is positioned above a horizontal plane defined by the tissue sample holder and terminates at an end within the container.

2. The biopsy device of claim 1, wherein the conduit is proximally held relative to the probe cannula by a tube guide.

3. The biopsy device of claim 1, wherein the conduit defines at least a portion of a fluid passageway.

4. The biopsy device of claim 3, further comprising a second fluid passageway, wherein the tissue sample holder includes a straining member, wherein the straining member defines the horizontal plane of the tissue sample holder, wherein the second fluid passageway passes through the plane defined by the straining member and terminates at a free end within the container.

5. The biopsy device of claim 3, further comprising a vacuum lumen communicating to a distal end of the probe cannula and a second conduit between the container and the vacuum lumen, wherein the second conduit is configured to communicate vacuum with the vacuum lumen, wherein the tissue sample holder includes a straining member, wherein the horizontal plane of the tissue sample holder is defined by the straining member.

6. The biopsy device of claim 5, wherein the second conduit passes through the plane defined by the straining member and terminates at a free end within the container.

7. The biopsy device of claim 5, wherein the second conduit is positioned above the plane defined by the straining member and terminates at a free end within the tissue sample holder.

8. The biopsy device of claim 6, further comprising a pneumatic switching assembly responsive to the cutter, wherein the pneumatic switching assembly is operatively configured to expose both the cutter and the vacuum lumen from the vacuum source in response to the cutter being retracted to prolapse tissue into the side aperture, wherein the pneumatic switching assembly is responsive to the cutter being distally positioned to expose the vacuum lumen to an increased pressure to effect retraction of severed tissue to the container via the conduit.

9. The biopsy device of claim 1, wherein the container defines a fluid reservoir, wherein at least a portion of the fluid reservoir is defined by the tissue sample holder.

10. The biopsy device of claim 9, wherein the tissue sample holder is configured to hold solid tissue samples separately from the fluid reservoir.

11. The biopsy device of claim 10, wherein the tissue sample holder includes a removable portion, wherein the removable portion of the tissue sample holder includes a basket.

12. The biopsy device of claim 11, wherein the basket is configured to hold solid tissue samples while permitting fluid to flow through the basket.

13. The biopsy device of claim 11, wherein the removable portion includes a straining member, wherein a vacuum port is positioned above the straining member.

14. The biopsy device of claim 1, further comprising a motor assembly operatively configured to translate the cutter to sever a tissue sample.

15. A biopsy system comprising:
   (a) a biopsy device including:
      (i) a body,
      (ii) a cannula defining an internal passage and having a side aperture, and
      (iii) a cutter translatable relative to the probe cannula to sever a tissue sample received in the probe cannula;
   (b) a sample collection assembly including:
      (i) a tissue sample holder extending entirely around an inner perimeter of a container such that the tissue sample holder is configured to separate solid tissue samples from fluid as vacuum is communicated through the container, wherein the tissue sample holder is further configured to hold tissue samples severed by the cutter; and
      (ii) a conduit extending from the tissue sample holder to the biopsy device; wherein the conduit is configured to communicate tissue samples from the biopsy device to the tissue sample holder, wherein at least a portion of the conduit includes a flexible tube coupling the sample collection assembly with the cannula such that the cannula is movable relative to the sample collection assembly; wherein at least a portion of the conduit includes an elbow portion, wherein the elbow portion is configured to direct tissue samples toward the tissue sample holder.

16. The biopsy system of claim 15, wherein the tissue sample holder further includes a lid, wherein the conduit is configured to engage the lid.

17. The biopsy system of claim 15, wherein the conduit terminates at a proximal end located above at least a portion of the tissue sample holder.

18. The biopsy system of claim 15, wherein the tissue sample holder includes a straining member, wherein the straining member includes a perforated portion.

19. The biopsy system of claim 15, further comprising a tube guide, wherein the tube guide is configured to hold at least a portion of the conduit proximally relative to at least a portion of the biopsy device.

20. The biopsy system of claim 15, further comprising a vacuum conduit, wherein the tissue sample holder includes a strainer, wherein the strainer defines a straining plane, wherein the vacuum conduit includes a proximal end that is disposed below the straining plane such that the vacuum conduit is configured to draw fluid through the strainer of the tissue sample holder.

21. The biopsy system of claim 15, wherein the container defines a fluid reservoir, wherein at least a portion of the fluid reservoir is defined by the tissue sample holder.

22. The biopsy system of claim 21, wherein the tissue sample holder is configured to hold solid tissue samples separately from the fluid reservoir.

23. The biopsy system of claim 15, wherein the tissue sample holder includes a removable portion, wherein the removable portion of the tissue sample holder includes a basket, wherein the basket is configured to hold solid tissue samples while permitting fluid to flow through the basket.

24. The biopsy system of claim 23, wherein the basket defines a strainer, wherein the basket is configured for removal from the container and for insertion into a formalin container.

25. The biopsy system of claim 15, wherein the tissue sample holder further includes a lid and a strainer, wherein the conduit is configured to engage the lid, wherein the straining member includes a perforated portion.

26. The biopsy system of claim 15, wherein the tissue sample holder further includes a lid and a removable portion, wherein the conduit is configured to engage the lid, wherein the removable portion includes a basket, wherein the basket includes a strainer such that the basket is configured to hold solid tissue samples while permitting fluid to flow through the basket, wherein the basket is configured for removal from the container and for insertion into a formalin container.

27. The biopsy system of claim 15, wherein the tissue sample holder further includes a lid and a removable portion, wherein the conduit is configured to engage the lid, wherein the removable portion includes a basket, wherein the basket includes a strainer such that the basket is configured to hold solid tissue samples while permitting fluid to flow through the basket, wherein the basket is configured for removal from the container and for insertion into a formalin container, wherein the container defines a fluid reservoir, wherein at least a portion of the fluid reservoir is defined by the tissue sample holder, the basket is configured to hold solid tissue samples separately from the fluid reservoir.

* * * * *